(12) United States Patent
Jiang et al.

(10) Patent No.: US 8,401,300 B2
(45) Date of Patent: Mar. 19, 2013

(54) TARGETED IMAGE TRANSFORMATION OF SKIN ATTRIBUTE

(75) Inventors: Zhi-xing Jiang, Southbury, CT (US); Matthew Benedict, Winsted, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 603 days.

(21) Appl. No.: 12/636,830

(22) Filed: Dec. 14, 2009

(65) Prior Publication Data

US 2011/0142305 A1 Jun. 16, 2011

(51) Int. Cl.
*G06K 9/46* (2006.01)
*G06K 9/66* (2006.01)

(52) U.S. Cl. ........ 382/190; 382/128; 382/169; 382/264; 600/306

(58) Field of Classification Search .................. 382/128, 382/162, 190, 195, 264; 600/306
See application file for complete search history.

(56) References Cited

U.S. PATENT DOCUMENTS

| | | | |
|---|---|---|---|
| 6,091,836 A | 7/2000 | Takano et al. | 382/118 |
| 6,571,003 B1 | 5/2003 | Hillebrand et al. | 382/118 |
| 6,734,858 B2 | 5/2004 | Attar et al. | 345/475 |
| 6,761,697 B2 | 7/2004 | Rubinstenn et al. | 600/587 |
| 6,959,119 B2 | 10/2005 | Hawkins et al. | 382/276 |
| 7,425,427 B2 * | 9/2008 | Hirai et al. | 435/40.5 |
| 7,539,342 B2 * | 5/2009 | Tabata et al. | 382/167 |
| 8,290,257 B2 * | 10/2012 | Demirli et al. | 382/165 |
| 2004/0261280 A1 | 12/2004 | Znaiden et al. | 33/494 |
| 2007/0086651 A1 * | 4/2007 | Stephan et al. | 382/162 |
| 2008/0304736 A1 | 12/2008 | Nakagawa et al. | 382/165 |
| 2009/0054744 A1 * | 2/2009 | Kitamura et al. | 600/306 |
| 2011/0142305 A1 * | 6/2011 | Jiang et al. | 382/128 |

FOREIGN PATENT DOCUMENTS

| | | |
|---|---|---|
| EP | 0516 457 | 12/1992 |
| WO | 2008/028893 | 3/2008 |
| WO | WO 2008028893 A1 * | 3/2008 |

OTHER PUBLICATIONS

Japanese Abstract 2007-252891—published Oct. 4, 2007.
Japanese Abstract 2002-330943—published Nov. 19, 2002.

* cited by examiner

*Primary Examiner* — Gregory M Desire
(74) *Attorney, Agent, or Firm* — Michael P. Aronson

(57) ABSTRACT

Targeted attribute transformation involves obtaining a digital image of the skin, selecting an individual skin attribute (an imperfection, such as a blemishes, pores, or wrinkles), extracting the individual skin attribute from the digital image by linear digital filtering on all the color channels, to obtain a contrast map in all three channels of the individual attribute, and adding or subtracting a fraction of the contrast map to the initial image, to obtain the skin image with transformed selected skin attribute.

8 Claims, No Drawings

TARGETED IMAGE TRANSFORMATION OF SKIN ATTRIBUTE

TECHNICAL FIELD

The present invention relates to extracting individual skin attributes from a digital skin image, and analysing, measuring and/or predicting/simulating the appearance of the skin, by manipulating one or more of the individually extracted attributes. The method is particularly useful in measuring the efficacy of skin treatment composition on one or more individual attributes.

BACKGROUND OF THE INVENTION

The desire to look young and healthy is universal. Primary attributes of young and healthy-looking skin are evenness of skin color and texture. Uneven skin color and texture is the result of one or more imperfections: lines and wrinkles, blotches and age spots, visible pores, etc. Assessment of the efficacy of compositions to correct imperfections of the skin is an important part of the activity in the development of skin products. One commonly used method for assessment of the blemishes is through use of professional clinical graders. In this method trained clinicians grade the improvement of the skin appearance over extended use of the product. This assessment is subjective and expensive. Hence there have been many attempts to use instrument based image analysis methods to objectively grade the skin appearance. See for instance EP 516 457 (Unilever); WO 2008/028893 (Unilever); Hillebrand et al., U.S. Pat. No. 6,571,003; Rubinstenn et al., U.S. Pat. No. 6,761,697; Attar et al., U.S. Pat. No. 6,734,858; Hawkins et al., U.S. Pat. No. 6,959,119; Takano et al., U.S. Pat. No. 6,091,836; U.S. Patent Application No. 2004/0261280; and U.S. Patent Application No. 2007/0086651 A1; JP 2007-252891 and JP 2002-330943 (abstracts).

SUMMARY OF THE INVENTION

The present invention is based at least in part on the finding that individual skin attributes (imperfections), e.g. just blemishes such as age spots or just pores or just lines and wrinkles, can be extracted from an initial digital image of the skin, digitally processed, and then digitally added to or subtracted from the initial digital image, to measure the effect of the treatment and/or to predict/simulate either improved or deteriorated skin appearance based on one or more extracted individual skin attributes.

DETAILED DESCRIPTION OF THE INVENTION

"Skin" as used herein, is meant to include skin on the face, neck, scalp, underarms, chest, back, arms, hands, legs, scalp, feet, buttocks and abdomen, preferably the hands, neck, face, and underarms. The invention is suitable for analyzing any skin type.

"Attribute" as used herein means skin imperfection, including blemishes (age spots, blotches), pores, lines and wrinkles, and grooves (the words "lines," "wrinkles," and grooves being used interchangeably herein).

"Age spots" as used herein means any hyperpigmentation (e.g. including solar lentigo), spots and/or freckles.

"Targeted Attribute Transform" or "TAT" as used herein means the extraction of an individual skin attribute/imperfection, making a contrast map thereof, and the addition or subtraction of a fraction of the contrast map to the original image to predict/simulate an improved (addition) or deteriorated (subtraction) condition of the skin. Individual TATs for different attributes can be combined, to provide a transformed image based on several TATs.

The method involves the use of a color digital camera and an image analysis means, e.g. a personal computer.

The measurement can be used to track the progress of a treatment for blemishes, pores or wrinkles on the skin over time and/or to predict/simulate either improved or deteriorated appearance of skin.

First a digital color image of the skin is taken. This is done using a color digital camera to get a digital image which is noise-free and of suitable resolution, typically from at least 3 pixels/mm to 150 pixels/mm, preferably from 5 pixels/mm to 70 pixels/mm, more preferably between 10 pixels/mm to 50 pixels/mm. The position of the camera is adjusted such that all the images are acquired at a fixed lighting condition. The image can be digitized as for instance 100×100, or 4096×3072, or 2048×1536 matrix of pixels where each pixel in the matrix has a color intensity value. The data is then transferred to a means for image analysis e.g. a personal computer.

A digital color image in the present invention must be composed of all the color channels: for example, red, green and blue channel or color channels in other formats such as $L^*$, $a^*$ and $b^*$ channels. By virtue of using all the color channels in the present invention, a more realistic and representative image of the skin is obtained as the starting point, and therefore a more realistic and representative the ultimate TAT. RGB (red, green, and blue) color space is preferred because the color images encoded in RGB channels from digital color cameras are readily available. The digital image is in the discrete domain where each pixel has an intensity value associated with it. There could be large discontinuities in the intensity values especially in areas having blemishes and/or pores and/or wrinkles. The discontinuities are usually represented by a dip in intensity in each color channel, for the targeted skin attribute. In order to facilitate the image processing computations, it has been found that optimum results are obtained when all the color channels are subjected to, preferably linear digital filter operation such as Gaussian filtering or averaging filtering. Gaussian filtering is preferred because Gaussian filter operations result in a blur that preserves boundaries and edges better. The filter operation is explained below.

Linear filtering is a mathematical technique well known in the art to blur the fine details of the digital image selectively within the image. Linear filtering can be applied in two dimensions (2-D) or in one dimension (1-D) depending on the desired effect of the blurring. The selection of the filter size and type is dependent on the size of the intensity dip in each color channel and the geometry of the attribute to be extracted. The larger the radius of the employed filter, the larger the scale of fine detail that will be blurred—small filters blur only very fine detail while large filters blur larger levels of detail.

In linear filtering, a convolution matrix (filter) is built from a pre-defined distribution, preferably a Gaussian (Gaussian filter) or a uniform (averaging filter) distribution, based on the distance of pixels from the center point. The convolution matrix is convolved with the original image to produce a blurred image. For example, when one applies a 2-D Gaussian filter with a radius of 3, (i.e. 6*6) on a 20*20 image matrix, each pixel in the 20×20 image is computed as the weighted average of the pixels in a 6×6 neighborhood around it. The weights are defined by the convolution matrix. If a Gaussian filter is used, the original pixel's value receives the heaviest weight (having the highest Gaussian value), and neighboring pixels receive smaller weights as their distance to the original pixel increases. If an averaging filter is used, each pixel in the neighborhood receives equal weight. Averaging filters are a special case of Gaussian filters in the limit of large standard deviations.

Gaussian and averaging filter operations are unique in that, in addition to being completely circularly symmetric, they can be applied to a two-dimensional image as two independent one-dimensional calculations. That is, the effect of applying the two-dimensional matrix can also be achieved by applying a series of single-dimensional Gaussian or averaging filters in the horizontal direction, then repeating the process in the vertical direction.

For blemishes and pores, 2-D Gaussian filtering is most effective. It has been observed that optimum results are obtained when an original image is subjected to two selective Gaussian filter operations. The resultant image of the difference between the Gaussian blurred images is the contrast map for the desired skin attribute, in this case skin blemishes. The radii for the both the fine and coarse filter operations are related to the size (in pixels) of the targeted skin feature and depend on the resolution of the image. The preferred radius of the fine filter operation for a typical resolution is in the range of 1 to 100, more preferably 1 to 20 and optimally 5-10. The preferred standard deviation of the fine filter is in the range of 1 to 100, more preferably 1 to 70 and optimally 5 to 50. The radius for the coarse filter operation is in the range of 5 to 100, more preferably 15 to 60 and optimally 50. The preferred standard deviation of the coarse filter is in the range of 5 to 120, more preferably 5 to 100 and optimally 5 to 50. For pores, the preferred radius for the fine filter operation is in the range of 1 to 20, more preferably 1 to 10 and optimally 2-5. The preferred radius for the coarse filter operation is in the range of 1 to 20, more preferably 5 to 15 and optimally 6-8.

For wrinkles, 1-D Gaussian filtering at designated angles of 0°, 45°, 90°, and 145° is most effective. It has been observed that optimum results are obtained when an original image is subjected to two selective 1-D Gaussian filter operations at each of the designated angles. The resultant images of the difference between the Gaussian blurred images for each of the angles are averaged to form the contrast map for the skin attribute of lines/wrinkles. The dimension of 1-D Gaussian for the filter operations is related to the size of the targeted skin feature and depends on the resolution of the image. For a typical image, the dimension of the finer filter is preferably in the range of 1 to 50, more preferably 1 to 20 and optimally 1 to 10. The preferred standard deviation of the fine filter is in the range of 1 to 100, more preferably 1 to 70 and optimally 3 to 50. The dimension of 1-D Gaussian for the coarse filter operation is in the range of 5 to 100, more preferably 10 to 60 and optimally 25 to 35. The preferred standard deviation of the coarse filter is in the range of 1 to 100, more preferably 1 to 70 and optimally 3 to 50.

According to the preferred embodiment of the invention, two copies of the selected original color image with a typical resolution of (for example: ~10 pixels/mm) are made and named Image1 and Image2.

For blemish contrast maps, the Image1 (for all of its three color channels) is subjected to a fine Gaussian filter operation of radius r=(for example, 9 pixels) to make Image 1a. Image 2 (for all of its three color channels) is then subjected to a coarse Gaussian filter operation of radius R=(for example, 50 pixels) to make Image 2a. The image 1a is then subtracted from the Image 2a for each of the corresponding color channels to make Image 3. This is the contrast map for blemish. The amount of skin blemishes may be depicted as a number of summing the intensity values of the total pixels, or by counting the number of pixels above a certain value.

For pore contrast maps, the same Gaussian filter operation is used as described above for blemishes, except both fine and coarse Gaussian filters of smaller radius are used (optimally from 1-6 for the fine, and from 5-15 for the coarse).

For wrinkle contrast maps, the Image1 (for all of its three color channels) is subjected to a fine Gaussian filter operation (preferably with dimension of from 1 to 10, more preferably from 2 to 8, optimally 3) at a number of discreet angles (2 to 8, preferably 4 discreet angles) to make Images 1_0°, 1_45°, 1_90° and 1_135°. Image 2 (for all of its three color channels) is then subjected to a coarse Gaussian filter operation of dimension from 15 to 50, preferably 20 to 35, optimally 30 at the same number of discreet angles that was used fine Gaussian filter operation, to make Images 2_0°, 2_45°, 2_90° and 2_135°. The image 1_angles is then subtracted from the Image 2_angles for each of the corresponding color channels and discreet angles of 0°, 45°, 90° and 135° to make Image 3_0°, 3_45°, 3_90° and 3_135° respectively. The average of the Image 3_0°, 3_45°, 3_90° and 3_135° is the contrast map, Image 3, for lines/wrinkles. The amount of skin attribute such as wrinkles may be depicted as a number by summing the intensity values of the total pixels or by counting the number of pixels above a chosen value typically from 1 to 10.

To perform targeted transform for that attribute, a fraction of the image 3 is then added to or subtracted from the original image to become Image 4. The fraction is in the range of 0.01 to 10, preferably 0.01 to 5, and most preferably 0.02 to 2. The fraction is selected, depending on the particular application of TAT. For instance, improvement in blemishes can be measured using TAT that is typically obtained after using skin treatment composition. Say, 20% improvement is typically obtained. Then when a consumer with blemishes on skin comes to a cosmetic counter, predicted/simulated skin improvement can be demonstrated by TAT by adding 20% of image 3 (i.e. fraction of 0.2). In another example, significant reduction of blemishes can be demonstrated by adding 1 times contrast map, i.e. at a fraction 1 or 100% of Image 3. For wrinkles, significant reduction may be demonstrated using even a slightly higher fraction at, i.e. 1.2. On the other hand, the worsening of a skin attribute can be predicted/simulated by subtracting 20% of Image 3, i.e. at a fraction of 0.2.

The invention also provides for the use of the Targeted Attribute Transformation sequentially on multiple attributes on the same image, to simulate/predict the effects of improving/worsening all of them at different transformation levels.

The invention also provides for a system for carrying out the method of the invention comprising means to acquire the digital image of the skin operatively connected to a means for carrying out the image processing.

The invention thus provides for a method and a system to measure and track the progress of targeted attributes on skin over time using digital images taken under standard lighting conditions.

The invention also includes using Targeted Attribute Transformation of the invention in evaluation and selection process for consumer products. The information collected from the assessment, including any answer or answers provided during the survey, may, for example, result in a recommended product for the panelist to utilize in order to improve the targeted characteristic, like evenness of color. Subsequent to utilizing the product recommended, the resulting treated skin is assessed for product efficacy and overall performance. Any and all information generated pre- and post-treatment may be stored and maintained, preferably, in a database and can be used in association with a symbol to market products.

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

What is claimed is:

1. A method of digitally transforming a skin image, the method comprising the following steps in sequence:
   (a) acquiring a digital image of the skin, to obtain a first image;
   (b) extracting an individual skin attribute selected from the group consisting of blemishes, pores, fine lines and wrinkles from the digital image by linear digital filtering on all color channels, to obtain a contrast map in all three channels of the individual attribute; wherein the contrast map in constructed by one or both of the following filtering procedures;
   i) for blemishes and pores, making two copies, designated copy 1 and copy 2 of the first image for each of its three color channels; subjecting copy 1 to a fine 2D Gaussian filter operation of radius r and subjecting copy 2 to a coarse 2D Gaussian filter operation of radius R to make two filtered images 1a and 2a respectively; subtracting image1a from the Image 2a for each of the corresponding color channels to make the contrast map for blemishes and pores;
   ii) for fine lines and wrinkles, making two copies of the first image for each of its three color channels, designated image 1 and image 2; subjecting image 1 to a fine 1D Gaussian filter operation at 4 discreet angles to make Images 1-0°, 1-45°, 1-90° and 1-135°; subjecting Image 2 for each of its three color channels to a coarse 1D Gaussian filter operation at the same discreet angles used in the fine 1D Gaussian filter operation so as to make Images 2-0°, 2-45°, 2-90° and 2-135°; subtracting at each angle images 1- from Images 2- for each of the corresponding color channels and the discreet angles of 0°, 45°, 90° and 135° so as to make Images 3-0°, 3-45°, 3-90° and 3-135° respectively; averaging Images 3-0°, 3-45°, 3-90°, and 3-135° to obtain the contrast map for fine lines and wrinkles; and
   (c) transforming the first image by adding to the first image or subtracting from the first image a fraction of the contrast map, to obtain a second image with transformed individual skin attribute.

2. A method of claim 1 wherein the method comprises adding a fraction up to a multiple of the contrast map in step (c) to the original image in step (a) to demonstrate predicted/simulated improvement of the skin appearance.

3. A method of claim 1 wherein the method comprises subtracting a fraction up to a multiple of the contrast map in step (c) from the original image in step (a), to demonstrate predicted/simulated worsening of the skin appearance.

4. A method of claim 1 wherein step (b) is repeated to obtain a contrast map of a second individual attribute.

5. A method of claim 4 wherein in step (c) the contrast maps of two or more individual attributes are added to obtain the second image combining two or more skin attribute transforms.

6. A method of claim 1, comprising additional steps of
   (i) treating the skin with a skin care product
   (ii) obtaining a digital image of the treated skin
   (iii) calculating the relative improvement
   (iv) and demonstrating the improvement in transformed images.

7. A method of claim 1 wherein the individual attribute of skin blemish or pore or wrinkle is quantified at various time points to track the progress of the treatment.

8. The method of claim 1 wherein the amount of skin blemishes, pores, fine lines and wrinkles is depicted as a number by summing intensity values of total pixels in the contrast map, or by counting number of pixels above a certain value.

* * * * *